(12) United States Patent
Janzen et al.

(10) Patent No.: US 12,035,726 B2
(45) Date of Patent: Jul. 16, 2024

(54) METHOD FOR PRODUCING A CHEESE WITH REDUCED AMOUNT OF GALACTOSE

(71) Applicant: Chr. Hansen A/S, Hoersholm (DK)

(72) Inventors: Thomas Janzen, Hoersholm (DK); Ditte Ellegaard Christiansen, Hoersholm (DK); Veronique Jactat, Hoersholm (DK); Kasper Rosenkvist, Hoersholm (DK); Charlotte Elisabeth Grüner Schöller, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 213 days.

(21) Appl. No.: 17/253,851

(22) PCT Filed: Jun. 20, 2019

(86) PCT No.: PCT/EP2019/066348
§ 371 (c)(1),
(2) Date: Dec. 18, 2020

(87) PCT Pub. No.: WO2019/243497
PCT Pub. Date: Dec. 26, 2019

(65) Prior Publication Data
US 2021/0259266 A1    Aug. 26, 2021

(30) Foreign Application Priority Data

Jun. 20, 2018 (EP) .................................. 18178708

(51) Int. Cl.
*A23C 19/032* (2006.01)
*A23C 19/068* (2006.01)
(Continued)

(52) U.S. Cl.
CPC ...... *A23C 19/0323* (2013.01); *A23C 19/0684* (2013.01); *C12N 1/205* (2021.05);
(Continued)

(58) Field of Classification Search
CPC ............ A23C 19/0323; A23C 19/0684; C12N 1/205; A23Y 2220/49; A23Y 2220/73;
(Continued)

(56) References Cited

U.S. PATENT DOCUMENTS 8,865,238 B2   10/2014  Janzen et al.
9,060,524 B2    6/2015  Janzen et al.
(Continued)

FOREIGN PATENT DOCUMENTS

CN       102307481 A     1/2012
WO    WO-2011/026863 A1  3/2011
(Continued)

OTHER PUBLICATIONS

Mukherjee K and Hutkins R, "Isolation of Galactose-Fermenting Thermophilic Cultures and Their Use in the Manufacture of Low Browning Mozzarella Cheese," 1994 J Dairy Sci 77:2839-2849 (Year: 1994).*

(Continued)

*Primary Examiner* — Donald R Spamer
*Assistant Examiner* — Jeffrey D Benson
(74) *Attorney, Agent, or Firm* — Yoshimi D. Barron

(57) ABSTRACT

A method for producing a cheese with reduced amount of galactose comprising inoculating milk with *Streptococcus thermophilus* Gal(+) bacteria and *Lactobacillus* Gal(+) Lac (−) bacteria.

14 Claims, 3 Drawing Sheets

Figure 1:
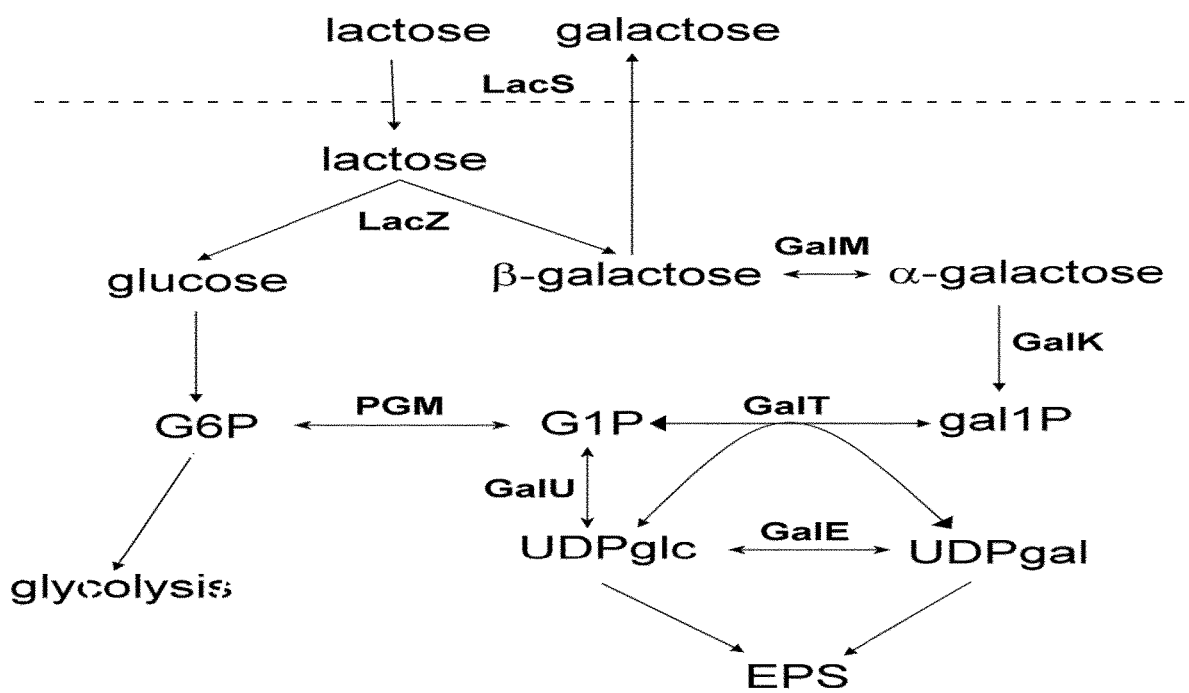

(51) Int. Cl.
*C12N 1/20* (2006.01)
*C12R 1/225* (2006.01)

(52) U.S. Cl.
CPC ... *A23V 2400/157* (2023.08); *A23V 2400/175* (2023.08); *A23V 2400/249* (2023.08); *C12R 2001/225* (2021.05)

(58) Field of Classification Search
CPC ............ A23Y 2240/75; A23Y 2220/63; C12R 2001/225
See application file for complete search history.

(56) References Cited

U.S. PATENT DOCUMENTS

| | | |
|---|---|---|
| 9,416,351 B2 | 8/2016 | Janzen et al. |
| 9,562,221 B2 | 2/2017 | Janzen et al. |
| 2012/0164275 A1 | 6/2012 | Janzen et al. |
| 2012/0301575 A1 | 11/2012 | Janzen et al. |
| 2015/0086675 A1 | 3/2015 | Johansen et al. |
| 2015/0099273 A1 | 4/2015 | Janzen et al. |
| 2015/0322415 A1 | 11/2015 | Janzen et al. |
| 2016/0227803 A1 | 8/2016 | Janzen et al. |
| 2017/0096635 A1 | 4/2017 | Janzen et al. |
| 2017/0298457 A1 | 10/2017 | Janzen et al. |
| 2019/0183160 A1 | 6/2019 | Gilleladen et al. |
| 2020/0093149 A1 | 3/2020 | Johansen et al. |
| 2020/0375207 A1 | 12/2020 | Janzen et al. |
| 2021/0259266 A1 | 8/2021 | Janzen et al. |

FOREIGN PATENT DOCUMENTS

| | | | | |
|---|---|---|---|---|
| WO | WO-2011/092300 A1 | | 8/2011 | |
| WO | WO-2013/160413 A1 | | 10/2013 | |
| WO | WO-2013160413 A1 | * | 10/2013 | ......... A23C 19/0323 |
| WO | WO-2015193449 A1 | * | 12/2015 | ........... A23C 9/1206 |
| WO | WO-2017103051 A1 | * | 6/2017 | ............. A23C 9/123 |
| WO | WO-2017/194650 A | | 11/2017 | |
| WO | WO-2017194650 A1 | * | 11/2017 | ............... A23C 9/12 |

OTHER PUBLICATIONS

Hassan et al., "Factors affecting capsule size and production by lactic acid bacteria used as dairy starter cultures", (International Journal of Food Microbiology 64 (2001) 199-203).

Mukherjee et al., "Isolation of Galactose-Fermenting Thermophilic Cultures and Their Use in the Manufacture of Low Browning Mozzarella Cheese", (1994, J Dairy Sci 77:2839-2849).

Anbukkarasi et al., "Production of low browning Mozzarella cheese: Screening and characterization of wild galactose fermenting *Streptococcus thermophilus* strains", International Journal of advanced research, 2013, vol. 1, No. 5, pp. 83-96 (Published online Jul. 2013).

Cui et al., "New Insights into Various Production Characteristics of *Streptococcus thermophilus* Strains", Int. J. Mol. Sci., vol. 17 (Oct. 2016).

De Vin et al., "Molecular and biochemical analysis of the galactose phenotype of dairy *Streptococcus thermophilus* strains reveals four different fermentation profiles", Applied and Environmental Microbiology, vo. 71, No. 7, (Jul. 2005) pp. 3659-3667.

Derkx et al., "The art of strain improvement of industrial lactic acid bacteria without the use of recombinant DNA technology", Microbial Cell Factories, 2014, 13(Suppl 1):S5; Aug. 29, 2014; pp. 1-13.

Mukherjee et al., "Isolation of Galactose-Fermenting Thermophilic Cultures and Their Use in the Manufacture of Low Browning Mozzarella Cheese", Journal of Dairy Science, vol. 77, No. 10, pp. 2839-2849, Oct. 1994.

Thomas et al., "Selection of Galactose-Fermenting *Streptococcus thermophilus* in Lactose-Limited Chemostat Cultures", Applied and environmental microbiology, (Jul. 1984) pp. 186-191.

U.S. Patent and Trademark Office; Non-Final Office Action; U.S. Appl. No. 16/642,787; dated Aug. 1, 2022; 16 pages.

Vaughan et al., "Activation of Silent gal Genes in the lac-gal Regulon of *Streptococcus thermophilus*", Journal of Bacteriology, (Feb. 2001) pp. 1184-1194.

* cited by examiner

ST CHCC4323

ST CHCC27912 +
LB CHCC3402

ST CHCC9861

ST CHCC27912 +

LB CHCC27906

METHOD FOR PRODUCING A CHEESE WITH REDUCED AMOUNT OF GALACTOSE

CROSS-REFERENCE TO RELATED APPLICATIONS IDC-A1,AMD

The present application is the U.S. National Stage of International Application PCT/EP2019/066348, filed Jun. 20, 2019, and claims priority to European Patent Application No. 18178708.6, filed Jun. 20, 2018.

FIELD OF THE INVENTION

The present invention relates to a method for producing a cheese with reduced amount of galactose comprising inoculating milk with *Streptococcus thermophilus* Gal(+) bacteria and *Lactobacillus* Gal(+) Lac(−) bacteria.

BACKGROUND ART

The food industry uses numerous bacteria, in particular lactic bacteria, in order to improve e.g. the taste and the texture of foods. In the case of the dairy industry, lactic acid bacteria are used intensively in order to bring about the acidification of milk (by fermentation) but also in order to e.g. texturize the product into which they are incorporated.

Starter culture composition/mixture to make mozzarella cheese generally comprises the lactic acid bacterium (LAB) *Streptococcus thermophilus* (ST)—it may sometimes also comprise e.g. relevant *Lactobacillus* strains.

A relatively high concentration of galactose can result in "browning" during heating of cheeses as it is often described when e.g. mozzarella cheese is produced by *S. thermophilus* (ST) for e.g. pizza production.

The browning phenomenon is believed to be due to the Maillard reaction where galactose as reducing sugar is reacting with amino acids/peptides.

Beside this major problem during pizza cheese production, excess amounts of free galactose can also lead to post acidification problems and imbalance in the flora of other dairy product, such as e.g. soft cheeses.

As known in the art, in the species *S. thermophilus* galactose is excreted via the lactose/galactose system (see schematic drawing of lac/gal metabolism in FIG. 1 herein). For 1 mol of lactose taken up by the cell 1 mol of galactose may be excreted.

Many pizza manufacturers bake pizza at temperatures >260° C. At these high temperatures the propensity of the cheese to brown excessively has become a particular concern to the mozzarella industry.

The article of Hassan et al. (International Journal of Food Microbiology 64 (2001) 199-203) describes that the ability of some strains of *S. thermophilus* (ST) to use galactose in capsule production could reduce browning of mozzarella cheese during baking by removing a source of reducing sugar.

WO2011/026863A1 (Chr. Hansen) and WO2011/092300A1 (Chr. Hansen) describe that *S. thermophilus* (ST) strains with mutations in the GalK (galactokinase) gene generate a higher viscosity in fermented milk. None of these two WO publications describe above discussed browning of mozzarella cheese related problem.

WO2013/160413A1 (Chr. Hansen) describes herein discussed *Streptococcus thermophilus* (ST) CHCC14994 strain, which was deposited on 3 Apr. 2012 under the accession No. DSM 25838. The CHCC14994 strain is described as a so-called "mother strain" suitable to be used as a starting strain for being mutated in order to obtain novel mutated strains with "mutation in the DNA sequence of the glcK gene". Accordingly, the CHCC14994/DSM25838 strain is not disclosed to be present/comprised in a starter culture composition nor to be used in the manufacturing of a food or feed product of interest (e.g. a dairy product).

The abstract of the article of Mukherjee et al. (1994, J Dairy Sci 77:2839-2849) reads: "The objectives of this study were to isolate galactose-fermenting, galactose nonreleasing strains of *Streptococcus* and *Lactobacillus* and to use these strains as starter cultures in the manufacture of low browning Mozzarella cheese".

As discussed the article, the isolated *Streptococcus thermophilus* and *Lactobacillus* strains are characterized as galactose-fermenting [Gal(+)] (see e.g. Table 2).

As known in the art, *Lactobacillus* is normally/naturally able to ferment lactose [i.e. Lac(+)] and in the above discussed article of Mukherjee was not screened/selected specifically for "not able to ferment lactose" [i.e. Lac(−)] *Lactobacillus* strains—accordingly, there is no reason to believe that the isolated *Lactobacillus* strains (e.g. JM21 and JM31—see e.g. Table 2) of the article of Mukherjee are *Lactobacillus* Lac(−) strains.

The article of Mukherjee reads on page 2847, right column: "During control and experimental treatments in this study, the lactose content also dropped markedly"—this implicitly may be seen as demonstrating that the isolated *Lactobacillus* strains of the article of Mukherjee are *Lactobacillus* Lac(+) strains.

In summary, none of the above discussed prior art documents describes a method for producing a cheese with reduced amount of galactose comprising inoculating milk with *Streptococcus thermophilus* (ST) Gal(+) bacteria and *Lactobacillus* (Lb.) Gal(+) Lac(−) bacteria.

SUMMARY OF THE INVENTION

The problem to be solved by the present invention is to provide a novel improved method for producing a cheese with reduced amount of galactose (to e.g. get less browning during heat treatment).

The solution is based on that the present inventors identified that by inoculating milk with *Streptococcus thermophilus* (ST) Gal(+) bacteria and *Lactobacillus* (Lb.) Gal(+) Lac(−) bacteria it is possible to obtain a significant reduction of galactose as compared to use of ST Gal(+) and Lb. Gal(+) Lac(+) as described in the prior art (see e.g. above discussion of the article of Mukherjee et al.).

As discussed in e.g. working Example 3 herein—by use of ST Gal(+) and Lb. Gal(+) Lac(−) according to the present invention it was possible to get 64% reduction of galactose as compared to use of ST Gal(+) and Lb. Gal(+) Lac(+) as described in the prior art.

It is submitted that without the knowledge of the present invention relating to this significant reduction of galactose, the skilled person would not have considered to use Lb. Gal(+) Lac(−) bacteria according to the present invention.

Without being limited to theory—one reason for that it would prima facie be considered unwanted to use Lb. Lac(−) bacteria relate to that the ability to ferment lactose (Lac(+)) is generally considered a useful property of *Lactobacillus* due to it may help in so-called acidification (reduction of pH).

A theory to explain the herein discussed significant reduction of galactose may be that the Lac(−) *Lactobacillus* are "forced" to use galactose for growth and thereby remove more galactose—i.e. both ST Gal(+) and Lb. Gal(+) Lac(-) remove the galactose.

In relation to this theory, one may in the present context denote the Lb. Gal(+) Lac(-) bacteria as so-called galactose "scavengers".

As discussed in working Examples herein—herein deposited ST strain CHCC4323 (registration number DSM 32826) is herein a so-called reference strain, which in short may be seen as a galactose negative ST Gal (-) reference strain that corresponds to a today commercially relevant used ST strain for making mozzarella cheese.

Accordingly, a first aspect of the invention relates to a method for producing a cheese with reduced amount of galactose comprising following steps:

(a): inoculating milk with:
  (I): *Streptococcus thermophilus* (ST) bacteria, characterized by that the ST bacteria are able to reduce by at least 10% the amounts of excreted galactose in milk as compared to reference ST CHCC4323 (DSM 32826) bacteria (herein termed "ST Gal(+) bacteria");
    wherein the comparative test is performed by that the ST bacteria are inoculated in skim cow milk 1% from overnight cultures and incubated for 18 hours at 37° C. and at the end of the fermentation samples are taken to measure galactose content in the fermented milk and thereby measure the reduction of excreted galactose compared to the reference CHCC4323;
  and
  (II): *Lactobacillus* (Lb.) bacteria, characterized by that the Lb. bacteria are able to ferment galactose but not able to ferment lactose (herein termed "Lb. Gal(+) Lac(-) bacteria");
    wherein "able to ferment galactose" is measured by that the Lb. bacteria are inoculated in MRS (De Man, Rogosa and Sharpe) medium containing 1% galactose as sole carbohydrate 1% from overnight cultures and incubated for 24 hours at 37° C. and at the end of the fermentation samples are taken to measure pH and if the pH has decreased by at least 0.5 then is the Lb. "able to ferment galactose" (herein termed "LB. Gal(+) bacteria"); and
    wherein "not able to ferment lactose" is measured by that the Lb. bacteria are inoculated in MRS medium containing 1% lactose as sole carbohydrate 1% from overnight cultures and incubated for 18 hours at 37° C. and at the end of the fermentation samples are taken to measure pH and if the pH has not decreased by more than 1.0 then is the Lb. "not able to ferment lactose" (herein termed "LB. Lac(-) bacteria");
  and
(b): fermenting the milk with the bacteria of (a); and
(c): making further adequate steps to finally end up with the produced cheese with reduced amount of galactose.

The ST Gal(+) bacteria test according to "(a) (I)" of the first aspect may be considered a herein relevant standard test that routinely can be performed by the skilled person.

It is believed that a number of the ST Gal(+) bacteria described in above discussed prior art would comply with the ST Gal(+) test—i.e. based on the prior art and herein provided technical information it may be considered as relatively routine work to obtain ST Gal(+) bacteria that comply with the comparative test of "(a) (I)" of the first aspect.

In working Example 1 herein is described a method to obtain different ST Gal(+) bacteria complying with the comparative test of step "(a) (I)" of the first aspect—i.e. the comparative test of step "(a) (I)" of the first aspect is preferably performed according to Example 1.

The Lb. Gal(+) Lac(-) bacteria test according to "(a) (II)" of the first aspect may be considered a herein relevant standard test that routinely can be performed by the skilled person.

It is believed that a number of the Lb. Gal(+) bacteria described in above discussed prior art (e.g. above discussed Mukherjee et al. article) would comply with the Lb. Gal(+) test—i.e. based on the prior art and herein provided technical information it may be considered as relatively routine work to obtain Lb. Gal(+) bacteria that comply with the comparative test of "(a) (II)" of the first aspect.

Working Example 2 herein disclose a method to obtain "Lb. Gal(+) Lac(-) bacteria" of step "(a) (II)" of the first aspect and the method may be considered as based on routine skills of the skilled person—i.e. based on the prior art and herein provided technical information it may be considered as relatively routine work to obtain Lb. Gal(+) Lac(-) bacteria that comply with the comparative test of "(a) (II)" of the first aspect. The test of step "(a) (II)" of the first aspect is preferably performed according to Example 2.

MRS (De Man, Rogosa and Sharpe) medium is a well know medium for growth of *Lactobacillus* (Lb.) bacteria (see e.g. de Man, J. D.; Rogosa, M.; Sharpe, M. E. (1960). "A Medium for the Cultivation of Lactobacilli". J Appl Bact. 23 (130-135)).

As known in the art, MRS medium normally contains (w/v):

1.0% peptone
1.0% beef extract
0.4% yeast extract
2.0% glucose
0.5% sodium acetate trihydrate
0.1% polysorbate 80 (also known as Tween 80)
0.2% dipotassium hydrogen phosphate
0.2% triammonium citrate
0.02% magnesium sulfate heptahydrate
0.005% manganese sulfate tetrahydrate
1.0% agar Accordingly and as understood by the skilled person in the present context—"MRS medium containing 1% galactose as sole carbohydrate" is simply MRS medium as above, wherein the "2.0% glucose" is changed to "1% galactose" and "MRS medium containing 1% lactose as sole carbohydrate" is simply MRS medium as above, wherein the "2.0% glucose" is changed to "1% lactose".

In working Example 2 herein was used MRS with a pH of around 6.8, which may be consider a normal/standard pH value for MRS in the present context—i.e. the pH value of the MRS shall be around pH 6.8.

Step (b) "fermenting the milk with the bacteria of (a)" and step (c) "making further adequate steps to finally end up with the produced cheese with reduced amount of galactose" of the first aspect may be made according to the art—i.e. these steps are well known to the skilled person and the skilled person knows how to perform them in relation to make a preferred cheese of interest (e.g. mozzarella cheese).

Embodiment of the present invention is described below, by way of examples only.

DRAWINGS

FIG. 1: Schematic drawing of lac/gal metabolism

Figure 2:
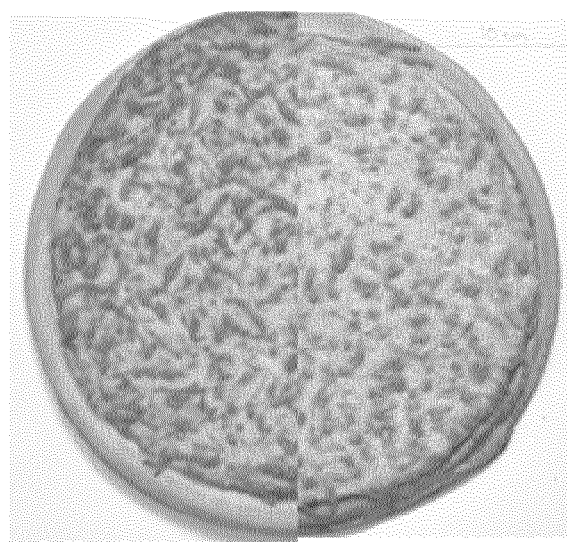

FIG. 2: The picture shows an evident difference in browning between control CHCC4323 and the browning reduction culture CHCC27912/CHCC3402 of the present invention. For further details see Example 4 herein.

Figure 3:
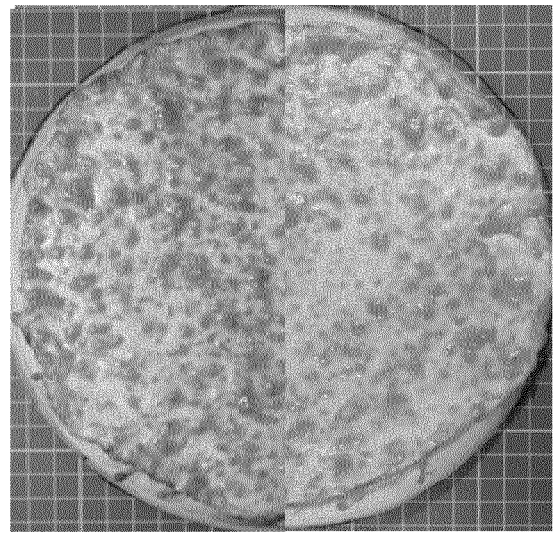

FIG. 3: The picture shows an evident difference in browning between the reference CHCC9861 and the experimental culture with CHCC27912/CHCC27906. For further details see Example 5 herein.

DETAILED DESCRIPTION OF THE INVENTION

Deposited Strains/Cells

A sample of the *Streptococcus thermophilus* cell CHCC14994 has been deposited at DSMZ (Deutsche Sammlung von Mikroorganismen und Zellkulturen GmbH, Inhoffenstr. 7B, D-38124 Braunschweig) under the accession number DSM 25838 with a deposit date of 3 Apr. 2012. The deposit has been made under the conditions of the Budapest Treaty on the International Recognition of the Deposit of Microorganisms for the Purposes of Patent Procedure.

A sample of the *Streptococcus thermophilus* cell CHCC19097 has been deposited at DSMZ (Deutsche Sammlung von Mikroorganismen und Zellkulturen GmbH, Inhoffenstr. 7B, D-38124 Braunschweig) under the accession number DSM 32594 with a deposit date of 22 Aug. 2017. The deposit has been made under the conditions of the Budapest Treaty on the International Recognition of the Deposit of Microorganisms for the Purposes of Patent Procedure.

A sample of the *Streptococcus thermophilus* cell CHCC19100 has been deposited at DSMZ (Deutsche Sammlung von Mikroorganismen und Zellkulturen GmbH, Inhoffenstr. 7B, D-38124 Braunschweig) under the accession number DSM 32595 with a deposit date of 22 Aug. 2017. The deposit has been made under the conditions of the Budapest Treaty on the International Recognition of the Deposit of Microorganisms for the Purposes of Patent Procedure.

A sample of the *Streptococcus thermophilus* cell CHCC27912 has been deposited at DSMZ (Deutsche Sammlung von Mikroorganismen und Zellkulturen GmbH, Inhoffenstr. 7B, D-38124 Braunschweig) under the accession number DSM 32596 with a deposit date of 22 Aug. 2017. The deposit has been made under the conditions of the Budapest Treaty on the International Recognition of the Deposit of Microorganisms for the Purposes of Patent Procedure.

A sample of the *Streptococcus thermophilus* cell CHCC29526 has been deposited at DSMZ (Deutsche Sammlung von Mikroorganismen und Zellkulturen GmbH, Inhoffenstr. 7B, D-38124 Braunschweig) under the accession number DSM 32597 with a deposit date of 22 Aug. 2017. The deposit has been made under the conditions of the Budapest Treaty on the International Recognition of the Deposit of Microorganisms for the Purposes of Patent Procedure.

A sample of the *Streptococcus thermophilus* cell CHCC29530 has been deposited at DSMZ (Deutsche Sammlung von Mikroorganismen und Zellkulturen GmbH, Inhoffenstr. 7B, D-38124 Braunschweig) under the accession number DSM 32598 with a deposit date of 22 Aug. 2017. The deposit has been made under the conditions of the Budapest Treaty on the International Recognition of the Deposit of Microorganisms for the Purposes of Patent Procedure.

A sample of the *Lactobacillus paracasei* cell CHCC6272 has been deposited at DSMZ (Deutsche Sammlung von Mikroorganismen und Zellkulturen GmbH, Inhoffenstr. 7B, D-38124 Braunschweig) under the accession number DSM 16572 with a deposit date of 13 Jul. 2004. The deposit has been made under the conditions of the Budapest Treaty on the International Recognition of the Deposit of Microorganisms for the Purposes of Patent Procedure.

A sample of the *Lactobacillus rhamnosus* cell CHCC3402 has been deposited under the accession number ATCC53103. This strain is commercially available under the trademark LGG® (https://www.igg.com/)—i.e. commercially available from e.g. Chr. Hansen A/S, Denmark.

The deposited strains below are strains that for the first time have been deposited in relation to the present application—i.e. they are novel strains as such.

A sample of the novel *Lactobacillus delbrueckii* subsp. *lactis* cell CHCC27906 has been deposited at DSMZ (Deutsche Sammlung von Mikroorganismen und Zellkulturen GmbH, Inhoffenstr. 7B, D-38124 Braunschweig) under the accession number DSM 32831 with a deposit date of 5 Jun. 2018. The deposit has been made under the conditions of the Budapest Treaty on the International Recognition of the Deposit of Microorganisms for the Purposes of Patent Procedure.

A sample of the novel *Streptococcus thermophilus* cell CHCC4323 has been deposited at DSMZ (Deutsche Sammlung von Mikroorganismen und Zellkulturen GmbH, Inhoffenstr. 7B, D-38124 Braunschweig) under the accession number DSM 32826 with a deposit date of 5 Jun. 2018. The deposit has been made under the conditions of the Budapest Treaty on the International Recognition of the Deposit of Microorganisms for the Purposes of Patent Procedure.

An aspect of the invention relates to a *Lactobacillus delbrueckii* subsp. *lactis* cell CHCC27906 deposited with registration number DSM 32831.

An aspect of the invention relates to a method to obtain a mutant strain *Lactobacillus delbrueckii* subsp. *lactis* cell CHCC27906 deposited with registration number DSM 32831 comprising using the deposited strain as starting strain, making mutants of the deposited strain and isolating a novel mutant strain, wherein the mutant strain has retained the property of being Lb. Gal(+) Lac(−) of the deposited strain.

Cheese

Preferably, the cheese is made by use of cow milk or goat milk (preferably cow milk)—i.e. the step (a) of first aspect preferably relates to inoculating cow or goat (preferably cow) milk with the ST Gal(+) bacteria and the Lb. Gal(+) Lac(−) bacteria.

In a preferred embodiment, the cheese is soft cheese, cheddar cheese, pasta filata cheese, pizza cheese or mozzarella cheese—more preferably, the cheese is pasta filata cheese, cheddar cheese, pizza cheese or mozzarella cheese—most preferably the cheese is mozzarella cheese (preferably used for making pizza), pizza cheese, or cheddar cheese (preferably used for making pizza).

As discussed above, a relatively high concentration of galactose can result in "browning" during heating of cheeses.

Accordingly, the cheese may preferably be a cheese used in a process (e.g. for making pizza) involving a heating step to a temperature above 40° C., such as above 50° C. or such as above 70° C.

As known in the art, for instance pasta filata cheese, pizza cheese and/or mozzarella cheese are examples of cheeses that may be used in a process involving a heating step to a temperature above 50° C.

As discussed above, many pizza manufacturers bake pizza at temperatures >260° C. Consequently, in a preferred embodiment the cheese (preferably pizza cheese) is a cheese used in a process involving a heating step to a temperature above 100° C., such as above 150° C. or such as above 200° C.

ST Gal(+) Bacteria of Step "(a) (I)" of First Aspect

In working Example 1 herein is described a method to obtain different ST Gal(+) bacteria complying with the comparative test of step "(a) (I)" of the first aspect.

As can be seen in Table 1 of Example 1, by use of the in this Example described special method for isolation of galactose hyper-fermenting mutants from S. thermophilus it was possible to obtain ST bacteria able to reduce by around 50% (see e.g. CHCC27912 and CHCC29526) the amounts of excreted galactose in milk as compared to reference ST CHCC4323 bacteria.

ST bacteria able to reduce by at least 20% the amounts of excreted galactose in milk as compared to reference ST CHCC4323 bacteria may herein be termed ST Gal(++) bacteria.

Without being limited to theory—the in Example 1 described special method for isolation of galactose hyper-fermenting ST Gal(++) mutants from S. thermophilus may be considered special due to the fact that the galactose reduction level is dramatically increased compared to a herein termed Gal(+) strain. As described in Example 1, the galactose reduction level for CHCC14993, a Gal(+) mutant of CHCC4323, is 17%, whereas the galactose reduction level of CHCC14994, a Gal(++) mutant of CHCC4323, is 30%, compared to the wild type CHCC4323. The galactose reduction level of CHCC29526, a Gal(++) mutant from CHCC4459, is even 52% compared to the reference CHCC4323.

By using the newly developed, not previously described method of sub-culturing in M17-gal broth it was therefore possible to isolate galactose hyper-fermenting mutants with a unique galactose reducing ability.

Preferably, the ST bacteria of step "(a) (I)" of the first aspect are ST bacteria characterized by that the ST bacteria are able to reduce by at least 20% (such as at least 25%, more preferably at least 30% and even more preferably least 40%) the amounts of excreted galactose in milk as compared to reference ST CHCC4323 bacteria.

Preferably, the *Streptococcus thermophilus* (ST) bacteria cell is at least one cell selected from the group consisting of:
  (a) a *Streptococcus thermophilus* cell CHCC19097 deposited with registration number DSM 32594;
  (b) a *Streptococcus thermophilus* cell CHCC19100 deposited with registration number DSM 32595;
  (c) a *Streptococcus thermophilus* cell CHCC27912 deposited with registration number DSM 32596;
  (d) a *Streptococcus thermophilus* cell CHCC29526 deposited with registration number DSM 32597;
  (e) a *Streptococcus thermophilus* cell CHCC29530 deposited with registration number DSM 32598; and
  (f): a *Streptococcus thermophilus* cell CHCC14994 deposited with registration number DSM 25838

Preferably, in step "(a) (I)" of the first aspect the milk is inoculated with from $10^4$ to $10^{15}$ cfu (or from $10^4$ to $10^{14}$ cfu) (colony forming units) viable ST bacteria cells per gram milk, including at least $10^5$ cfu per gram milk, such as at least $10^6$ cfu/g milk, such as at least $10^7$ cfu/g milk, such at least $10^8$ cfu/g milk, such as at least $10^9$ cfu/g milk, such as at least $10^{10}$ cfu/g milk or such as at least $10^{11}$ cfu/g milk.

The ST bacteria cells may be a mixture of different ST strains (e.g. a mixture of herein discussed CHCC27912 and CHCC29526)—for instance $10^8$ cfu/g milk of one ST strain (e.g. CHCC27912)+$10^8$ cfu/g milk of another ST strain (e.g. CHCC29526), which in sum would imply that the milk is inoculated with $2\times10^8$ cfu/g milk viable ST bacteria cells.

Typically, the bacteria (e.g. a starter culture composition) are in a concentrated form including frozen, dried or freeze-dried concentrates.

Lb. Gal(+) Lac(−) Bacteria of Step "(a) (II)" of First Aspect

Preferably, the *Lactobacillus* (Lb.) bacteria of step "(a) (II)" of first aspect are *Lb. helveticus* bacteria, *Lb. delbrueckii* bacteria, *Lb. paracasei* bacteria, *Lb. rhamnosus* bacteria or a mixture of these.

More preferably, the *Lactobacillus* (Lb.) bacteria of step "(a) (II)" of first aspect are *Lb. delbrueckii* bacteria, *Lb. paracasei* bacteria, *Lb. rhamnosus* bacteria or a mixture of these.

Even more preferably, the *Lactobacillus* (Lb.) bacteria of step "(a) (II)" of first aspect are Lb. *delbrueckii* bacteria—in particular *Lactobacillus delbrueckii* subsp. *lactis* bacteria.

As discussed above, working Example 2 herein disclose a method to obtain "Lb. Gal(+) Lac(−) bacteria" of step "(a) (II)" of the first aspect and the method may be considered as based on routine skills of the skilled person—i.e. based on the prior art and herein provided technical information it may be considered as relatively routine work to obtain Lb. Gal(+) Lac(−) bacteria that comply with the comparative test of "(a) (II)" of the first aspect.

The test of step "(a) (II)" of the first aspect is preferably performed according to Example 2.

With respect to Lb. Gal(+) element of step "(a) (II)" of first aspect it may generally be preferred that the bacteria are as good as possible to be able to ferment galactose.

Accordingly, in a preferred embodiment the Lb. Gal(+) related "able to ferment galactose" criteria of step "(a) (II)" of first aspect is only fulfilled "if the pH has decreased by at least 0.7", more preferably "if the pH has decreased by at least 0.9".

With respect to Lb. Lac(−) element of step "(a) (II)" of first aspect it may generally be preferred that the bacteria are essentially not able to ferment lactose at all.

Accordingly, in a preferred embodiment the Lb. Lac(−) related "not able to ferment lactose" criteria of step "(a) (II)" of first aspect is only fulfilled "if the pH has not decreased by more than 0.9", more preferably "if the pH has not decreased by more than 0.6" and even more preferably "if the pH has not decreased by more than 0.3".

Preferably, the *Lactobacillus* (Lb.) bacteria cell is at least one cell selected from the group consisting of:
  *Lactobacillus rhamnosus* CHCC3402, deposit number ATCC53103 (LGG® (https://www.lgg.com/));
  *Lactobacillus paracasei* CHCC6272, deposit number DSM 16572; and *Lactobacillus delbrueckii* ssp. *lactis* CHCC27906, deposit number DSM 32831.

Preferably, in step "(a) (II)" of the first aspect the milk is inoculated with from $10^4$ to $10^{15}$ cfu (or from $10^4$ to $10^{14}$ cfu) (colony forming units) viable Lb. bacteria cells per gram milk, including at least $10^5$ cfu per gram milk, such as at least $10^6$ cfu/g milk, such as at least $10^7$ cfu/g milk, such at least $10^8$ cfu/g milk, such as at least $10^9$ cfu/g milk, such as at least $10^{10}$ cfu/g milk or such as at least $10^{11}$ cfu/g milk.

The Lb. bacteria cells may be a mixture of different Lb. strains—for instance $10^8$ cfu/g milk of one Lb. strain+$10^8$ cfu/g milk of another Lb. strain, which in sum would imply that the milk is inoculated with $2\times10^8$ cfu/g milk viable Lb. bacteria cells.

Typically, the bacteria (e.g. a starter culture composition) are in a concentrated form including frozen, dried or freeze-dried concentrates.

Preferably, the ST Gal(+) bacteria and Lb. Gal(+) Lac(−) bacteria are inoculated together (e.g. together in a single composition—alternatively termed a co-culture) to the milk.

Fermenting the Milk with the Bacteria—Step (b) of First Aspect Step (b) of first aspect relates to fermenting the milk with the bacteria of (a).

As discussed above, the skilled person knows how to ferment milk with relevant bacteria to make a cheese of interest—accordingly, there is in the present context no need to describe this in great detail.

According to the art, the fermentation time in step (b) of the first aspect may be from 1 to 96 hours, such as from 2 to 72 hours or such as from 3 to 48 hours.

Further Adequate Steps to Make Cheese of Interest—Step (c) of First Aspect

Step (c) of first aspect relates to making further adequate steps to finally end up with the produced cheese of interest.

As discussed above, the skilled person knows how to make a preferred cheese of interest (e.g. mozzarella cheese)—accordingly, there is no need to describe this in great detail in the present context.

Separate Aspect of the Invention

As discussed above, a theory to explain the herein discussed significant reduction of galactose may be that the Lac(−) *Lactobacillus* are "forced" to use galactose for growth and thereby remove more galactose—i.e. both ST Gal(+) and Lb. Gal(+) Lac(−) remove the galactose.

In relation to this theory, one may in the present context denote the Lb. Gal(+) Lac(−) bacteria as so-called galactose "scavengers".

Without being limited to theory—one may say that prima facie there is no immediately evident reason for that above "scavengers" theory should not also be applicable for other lactic acid bacteria such as e.g. *Streptococcus thermophilus* (ST) bacteria. Accordingly, a separate aspect of the invention relates to a method for producing a cheese with reduced amount of galactose comprising following steps:

(a): inoculating milk with:

(I): *Streptococcus thermophilus* (ST) bacteria, characterized by that the ST bacteria are able to reduce by at least 10% the amounts of excreted galactose in milk as compared to reference ST CHCC4323 (DSM 32826) bacteria (herein termed "ST Gal(+) bacteria");

wherein the comparative test is performed by that the ST bacteria are inoculated in skim cow milk 1% from overnight cultures and incubated for 18 hours at 37° C. and at the end of the fermentation samples are taken to measure galactose content in the fermented milk and thereby measure the reduction of excreted galactose compared to the reference CHCC4323;

and (B): ST bacteria, characterized by that the ST bacteria are able to ferment galactose but not able to ferment lactose (herein termed "ST Gal(+) Lac(−) bacteria");

wherein "able to ferment galactose" is measured by that the ST bacteria are inoculated in M17 medium containing 2% galactose as sole carbohydrate 1% from overnight cultures and incubated for 16 hours at 37° C. and at the end of the fermentation samples are taken to measure pH and if the pH has decreased by at least 1.0 then is the ST "able to ferment galactose" (herein termed "ST Gal(+) bacteria");

and wherein "not able to ferment lactose" is measured by that the ST bacteria are inoculated in milk without addition of sucrose 1% from overnight cultures and incubated for 18 hours at 37° C. and at the end of the fermentation samples are taken to measure pH and if the pH has not decreased by more than 0.5 then is the ST "not able to ferment lactose" (herein termed "ST Lac(−) bacteria");

and (b): fermenting the milk with the bacteria of (a); and (c): making further adequate steps to finally end up with the produced cheese with reduced amount of galactose.

Similar to Lb. Gal(+) Lac(−) bacteria it is relatively routine work for the skilled person to obtain ST Gal(+) Lac(−) bacteria. In working Example 6 is shown data for a ST Gal(+) Lac(−) bacteria complying step "(a) (B)" of the separate aspect and obtained by a routine screening/selection method that one may say is similar to Example 2 herein.

With respect to ST Gal(+) element of step "(a) (II)" of separate aspect it may generally be preferred that the bacteria are as good as possible to be able to ferment galactose.

Accordingly, in a preferred embodiment the ST Gal(+) related "able to ferment galactose" criteria of step "(a) (II)" of separate aspect is only fulfilled "if the pH has decreased by at least 1.3", more preferably "if the pH has decreased by at least 1.6".

With respect to ST Lac(−) element of step "(a) (II)" of separate aspect it may generally be preferred that the bacteria are essentially not able to ferment lactose at all.

Accordingly, in a preferred embodiment the ST Lac(−) related "not able to ferment lactose" criteria of step "(a) (II)" of first aspect is only fulfilled "if the pH has not decreased by more than 0.4", more preferably "if the pH has not decreased by more than 0.3" and even more preferably "if the pH has not decreased by more than 0.1".

As understood by the skilled person in the present context—herein relevant preferred embodiments (e.g. preferred cheese, preferred cfu per gram milk, etc) of point "(a) (II)" of the first aspect are also preferred embodiments of point "(a) (B)" of the separate aspect.

For instance, also for the separate aspect—in a preferred embodiment, the cheese is soft cheese, cheddar cheese, pasta filata cheese, pizza cheese or mozzarella cheese—more preferably, the cheese is pasta filata cheese, cheddar cheese, pizza cheese or mozzarella cheese—most preferably the cheese is mozzarella cheese (preferably used for making pizza), pizza cheese, or cheddar cheese (preferably used for making pizza).

Preferably, in step "(a) (B)" of the separate aspect the milk is inoculated with from $10^4$ to $10^{15}$ cfu (or from $10^4$ to $10^{14}$ cfu) (colony forming units) viable ST bacteria cells per gram milk, including at least $10^5$ cfu per gram milk, such as at least $10^6$ cfu/g milk, such as at least $10^7$ cfu/g milk, such at least $10^8$ cfu/g milk, such as at least $10^9$ cfu/g milk, such as at least $10^{10}$ cfu/g milk or such as at least $10^{11}$ cfu/g milk.

EXAMPLES

Example 1: ST Gal(+) Bacteria—Capable of Extraordinary Reducing the Release of Galactose Also in the Presence of High Amounts of Lactose (as in Milk)—i.e. ST Gal(+) Bacteria of Step "(a) (I)" of the First Aspect Reference Strains:
ST strain CHCC4323: It has what may be termed a GalK natural wildtype sequence (herein termed GalK(−)) and may be seen as a ST reference strain that corresponds to a today commercially relevant used ST strains for making mozzarella cheese;
ST strain 4323-2 (CHCC14993): It comprises a mutation in the GalK (galactokinase) gene (herein termed Gal (+)) and may be seen as a reference strain that corresponds to a strain made according to the description of above discussed WO2011/026863A1 (Chr. Hansen) and WO2011/092300A1 (Chr. Hansen).
Deposited Strains:
CHCC14994: DSM 25838 ST strain—disclosed in WO2013/160413A1 (Chr. Hansen).
CHCC19097: Novel DSM 32594 ST strain as described herein.
CHCC19100: Novel DSM 32595 ST strain as described herein.
CHCC27912: Novel DSM 32596 ST strain as described herein.
CHCC29526: Novel DSM 32597 ST strain as described herein.
CHCC29530: Novel DSM 32598 ST strain as described herein.
Isolation of Galactose Hyper-Fermenting Mutants from *S. thermophilus*:
Prior to the mutant isolation the strains were streaked on M17 agar plates with 2% galactose (M17-gal plates). The wild type (wt) strains did not grow significantly on galactose as sole carbohydrate source.
Overnight cultures were then plated on M17-gal plates and several colonies could be isolated after two days of growth at 37° C. Several mutants were purified on M17-gal plates and retested in M17 broth containing 2% galactose as sole carbohydrate.
From purified galactose positive mutants second generation galactose hyper-fermenting mutants were isolated by sub-culturing in M17-gal broth with daily 1% re-inoculation from the fully outgrown overnight culture; incubation occurred at 37° C.
After dilution plating, 100 single colonies were isolated from M17-gal plates and inoculated in microtitre plates with M17-gal broth. The OD was followed by an OD-reader and the clones showing a better increase of OD during 16 hours of incubation at 37° C. as the wt strain were further purified and characterized.
The wt *S. thermophilus* strains from which galactose-hyperfermenting mutants were isolated are:
CHCC9861
CHCC4459
CHCC4426
CHCC4323
CHCC7018
CHCC3050
The galactose-hyperfermenting mutants showing an unusually high galactose fermenting ability and reduced galactose excretion into the media are (mutant/wt):

CHCC27912/CHCC9861
CHCC29526/CHCC4459
CHCC29530/CHCC4426
CHCC14994/CHCC4323
CHCC19100/CHCC7018
CHCC19097/CHCC3050

The example includes also a typical galactose positive strain, isolated as first generation mutant from CHCC4323, named CHCC14993. CHCC14993 showed a typical galactose reduction in milk of 17% (reduction of galactose excretion in milk compared to wt CHCC4323).
Fermentation of Milk
Mutant strains were inoculated in skim cow milk 1% from overnight cultures and incubated for 24 hours at 37° C. The acidification activity of mutants was similar to the wt strain. At the end of fermentation samples were taken to measure galactose content in the fermented milk and with this the reduction of excreted galactose compared to the galactose negative reference strain CHCC4323 and reference strain 4323-2 (CHCC14993).
Results—Analysis of Acidification and Excreted Galactose in the Fermented Milk
All the tested ST strains had similar acidification profiles—i.e. the deposited ST strains of the present invention had not lost their capacity to acidify fast in milk.
The amounts of excreted galactose for the different tested strains are shown in Table 1 below:
Table 1 indicates the amount of galactose in fermented skim cow milk and the reduction of galactose compared to the reference CHCC4323. Whereas the typical gal+mutant CHCC14993 showed a galactose reduction of less than 20%, the hyper-fermenting mutants showed a much higher reduction of up to 52%, meaning that the amount of free galactose is much lower when e.g. pizza cheese is produced with the new mutants, which is leading to reduced browning during baking.

TABLE 1

Average of two measurements from carbohydrate analysis. Results are shown in mg/g.

| Strain | Galactose | Galactose reduction (%) |
|---|---|---|
| CHCC4323 | 7.1 | 0 |
| CHCC14993 | 5.9 | 17 |
| CHCC27912 | 3.4 | 52 |
| CHCC29526 | 3.4 | 52 |
| CHCC29530 | 4.9 | 31 |
| CHCC14994 | 5.0 | 30 |
| CHCC19100 | 4.1 | 42 |
| CHCC19097 | 5.1 | 28 |

CONCLUSIONS

The results demonstrated that the herein deposited strains of the present invention are capable of reducing the release of galactose also in the presence of high amounts of lactose (as in milk) to a degree, which is extraordinarily improved as compared to above discussed reference strains.

Example 2: A Method to Obtain "Lb. Ga/(+) Lac(−) Bacteria" of Step "(a) (II)" of the First Aspect—MRS Criteria

*Lactobacillus delbrueckii* ssp. *lactis* CHCC27906 was isolated as lactose negative mutant of the lactose positive (and galactose positive) wild type strain *Lactobacillus delbrueckii* ssp. *lactis* CHCC14951.

Cells from CHCC14951 were UV-mutagenized with a UV-cross linker (Energy 120MJ). Cells which achieved a lethality of 99% (60 min UV-treatment) were plated on MRS-agar plates containing X-Gal. Due to beta-galactosidase activity lactose positive colonies appear blue, whereas lactose negative mutants grow as white colonies.

A range of putative lactose negative colonies were purified and retested in MRS where 1% lactose, respectively 1% glucose, was added as sole carbohydrate.

With a start pH of 6.8 CHCC14951 and the lactose negative mutant CHCC27906 reached a final pH of 4.2 after 18 hours at 37° C. in MRS-glucose. CHCC14951 acidified in a similar way in MRS-lactose broth, but the final pH for CHCC27906 in MRS-lactose was 6.6 after 18 hours, showing that CHCC27906 is a lactose negative mutant.

The genome analysis of CHCC27906 revealed a mutation at position 733 of lacZ (deletion of one nucleotide A), resulting in a truncated lacZ gene which explains the lactose negative phenotype.

When grown in MRS-galactose (MRS with 1% galactose as sole carbohydrate) under the conditions given above—CHCC27906 reached a pH of 5.8 after 24 hours at 37° C.

Conclusion

The results demonstrate that the mutant CHCC27906 is a Lb. Gal(+) Lac(-) bacterium, which complies with the criteria of (a)(II) of the first aspect (claim 1) herein. The wild type Lb. CHCC14951 strain is Lb. Gal(+) Lac(+) bacterium—i.e. it does not comply with the "not able to ferment lactose" criteria of (a)(II) of the first aspect (claim 1).

Example 3: Use of a Co-Culture of ST Gal(+) and Lb. Gal(+) Lac(-) According to the Present Invention Gave a Significant Higher % Reduction of Galactose in Milk as Compared to Use of ST Gal (+) Alone or Use of a Co-Culture of ST Gal(+) and Lb. Gal(+) Lac(+) According to the Art Fermentation of Milk ST strains were grown as overnight culture in M17, whereas lactose negative Lb strains were preincubated overnight in MRS broth to receive a fully grown culture. For the co-culture experiments the ST strains were inoculated 1% in milk (pasteurized at 98° C./30 min, 9.5% total solids) from the overnight cultures when grown alone. In mixed cultures the inoculation percentage was 0.75% for the ST plus 0.25% for the Lb Gal(+) Lac(-) or Lb Gal(+)Lac(+) strains.

Incubation occurred for 16 hours at 37° C. At the end of fermentation samples were taken to measure galactose content in the fermented milk and with this the reduction of excreted galactose compared to the galactose negative reference strain CHCC4323.

The lactose negative *Lactobacillus* strains are not able to acidify the milk significant. They can only grow on galactose excreted due to the lac/gal antiporter of the STs. Therefore they are "forced" to metabolize the available galactose. In the presence of both carbohydrates lactose and galactose as fermentable sugar the lactose is often preferred metabolized by lactic acid bacteria which would result in minor reduction of galactose as a specific time.

Results—Analysis of Acidification and Excreted Galactose in the Fermented Milk

The amounts of excreted galactose for the different tested strains are shown in Table 1 below:

Table 1 indicates the amount of galactose in milk and the reduction of galactose compared to the reference CHCC4323. The addition of the lactose negative scavengers CHCC3402, CHCC6272 or CHCC27906 leads to a reduction of galactose by 11%, 11%, and 9% respectively compared to the reference CHCC4323.

The addition of the lactose negative scavengers CHCC3402, CHCC6272 or CHCC27906 to CHCC27912, which has already the extraordinary capacity to decrease galactose reduction by 50% compared to CHCC4323, leads to a reduction of galactose by 66%, 73%, and 64% respectively, compared to the reference CHCC4323. Compared to the use of CHCC27912 the galactose content at the end of fermentation can thereby be reduced by additional 16%, 23% and 16% respectively. The use of the lactose negative scavengers is then even more efficient when co-cultured together with a galactose hyper fermenting strain compared to a galactose negative ST. When CHCC4323 or CHCC27912 is used in combination with CHCC14951, the lactose positive mother strain of CHCC27906, no reduction of galactose was measured.

In this Example was used a single colony isolate from CHCC14951 which is the direct mother strain for CHCC27906.

As a result the amount of free galactose is much lower when e.g. pizza cheese is produced with mixed cultures including the Lac(-) Gal(+) scavengers which is leading to reduced browning during baking.

TABLE 1

Average from two measurements from carbohydrate analysis. Results are shown in mg/g.

| Strain | Galactose | Galactose reduction (%) |
|---|---|---|
| CHCC4323 | 7.0 | 0 |
| CHCC27912 | 3.5 | 50 |
| CHCC3402 | <0.4 | No acidification |
| CHCC6272 | <0.4 | No acidification |
| CHCC27906 | <0.4 | No acidification |
| CHCC4323 + CHCC14951 | 8.4 | 0 |
| CHCC27912 + CHCC14951 | 6.9 | 0 |
| CHCC4323 + CHCC3402 | 6.2 | 11 |
| CHCC4323 + CHCC6272 | 6.2 | 11 |
| CHCC4323 + CHCC27906 | 6.4 | 9 |
| CHCC27912 + CHCC3402 | 2.4 | 66 |
| CHCC27912 + CHCC6272 | 1.9 | 73 |
| CHCC27912 + CHCC27906 | 2.5 | 64 |

Conclusions

The results demonstrated that the herein used strains of the present invention are capable of reducing the release of galactose also in the presence of high amounts of lactose (as in milk) to a degree, which is extraordinary improved as compared to above discussed reference strain.

CHCC27912 is a "ST Gal(+) bacteria" of (a)(I) of the first aspect (claim 1); CHCC27906 is a "Lb. Gal(+) Lac(-) bacteria" of (a)(I) of the first aspect (claim 1); CHCC14951 is the direct mother "Gal(+) Lac(+)" strain for CHCC27906.

Since the "CHCC27912+CHCC27906" result of "2.5 mg/g Galactose" is significantly below the "6.9 mg/g Galactose" result for "CHCC27912+CHCC14951"—this Example 3 demonstrates that by use of ST Gal(+) and Lb. Gal(+) Lac(-) according to the present invention it was possible to get 64% reduction of galactose as compared to use of ST Gal(+) and Lb. Gal(+) Lac(+) as described in the prior art.

Example 4: Pizza Cheese Making Using a Co-Culture of ST Gal(+) and Lb. Rhamnosus Gal(+) Lac(−) According to the Present Invention Strains *Streptococcus thermophilus* (ST) CHCC4323 (galactose negative) and CHCC27912 (galactose positive) were propagated in M17 media added 2% of galactose and incubated overnight at 37° C. Each pre-inoculum was then inoculated 0.05% in B-milk (pasteurized at 98° C./30 min, 9.5% total solids) and incubated 16 hours at 37° C.

In parallel, *Lactobacillus rhamnosus* CHCC3402 (lactose negative, galactose positive) was propagated in MRS media added with 2% of galactose and incubated overnight at 37° C. Each pre-inoculum was then used to inoculate 0.05% in the same media and incubated 40 hours at 37° C.

The starter culture used as a negative control for browning evaluation was the propagated culture of strain ST CHCC4323 in B-milk. A dose of 1% (w/w) of this bulk was then added to fermentation vat 1 containing 150 kg of cheese milk. The starter culture used to reduce browning was a combination of propagated cultures of ST CHCC27912 and *Lactobacillus rhamnosus* CHCC3402. The dose of these propagated cultures added to vat 2 were respectively 1.6% (w/w) and 0.4% (w/w). Cell counts from material taken just after inoculation was 1E+07 cells/mL for ST CHCC4323 and ST CHCC27912, and 1E+05 cells/mL for *Lactobacillus rhamnosus* CHCC3402. The milk composition was as follows: 2.70 (+/−0.05%) % of fat, 3.60 (+/−0.05%) of total protein and 4.60% (+/−0.05%) of lactose.

The hot maturation step was 60 min at 34.5° C. and the firmness at cutting was monitored by the CHYMO-Graph® (patented tool by Chr. Hansen®), the firmness index at cutting was 6.5. After cutting, the curd was pre-stirred for 10 minutes before scalding at 41° C. The scalding took 30 min and afterwards the curd was stirred for 20 min before the whey off step. The pH of the curd at whey-off was between 6.00 and 6.10. Afterwards, the curd was formed into blocks and turned 3 times before milling. The pH at milling was 5.17 (±0.02). After the milling, the curd was salted with 2% of dry salt before stretching and cheese cooling.

Residual galactose measured in the cheeses after 21 days shows a reduction of 49.4% (8.1 mg/g for control strain CHCC4323, vs. 4.1 mg/g for the mixed culture of CHCC27912 and CHCC3402).

After 30 days of storage (at 4° C.), the browning ability was compared by baking pizzas in a pizza oven for 3.5 min at 242° C. To prepare the pizzas, 40 g of tomato sauce was spread on the surface of frozen pizza dough and 135 g of coarse shredded cheese was distributed evenly on top. FIG. 2 herein shows an evident difference in browning between control CHCC4323 and the browning reduction culture CHCC27912/CHCC3402.

Example 5: Pizza Cheese Making Using a Co-Culture of ST Gal(+) and *Lb. Delbrueckii* Spp. *Lactis* Gal(+) Lac(−) According to the Present Invention

*S. thermophilus* CHCC9861 (galactose negative) and *S. thermophilus* CHCC27912 (galactose positive) were propagated in M17 media added 2% galactose and incubated overnight at 37° C. Each pre-inoculum was then inoculated 0.05% in B-milk (pasteurized at 98° C./30 min, 9.5% total solids) and incubated for 16 hours at 37° C.

In parallel, a pre-inoculum of *Lactobacillus delbrueckii* ssp. *lactis* CHCC27906 (lactose negative, galactose positive mutant isolated from a lactose positive wild type strain) was propagated in MRS media with 2% galactose and incubated overnight at 37° C. was used to inoculate with 0.05% in the same media and incubated 40 hours at 37° C.

The starter culture used as a negative control for browning evaluation was ST CHCC9861 (galactose negative). A dose of 2% (w/w) of this bulk was added to vat 1 containing 150 kg of cheese milk. The starter culture used to reduce browning was a combination of propagated cultures of ST CHCC27912 and *Lactobacillus delbrueckii* ssp. *lactis* CHCC27906. The dose of these propagated cultures added to vat 2 were respectively 1.5% (w/w) and 0.5% (w/w). Cells counts from material taken just after inoculation were 1E+07 cells/mL for ST CHCC9861 and ST CHCC27912, and 1E+05 cells/mL for *Lactobacillus delbrueckii* ssp. *lactis* CHCC27906.

The milk composition was as follow: 2.80 (+/−0.05%) % of fat, 3.80% (+/−0.05%) of total protein and 4.80% (+/−0.05%) of lactose.

The hot maturation step was 60 min at 34.5° C. and the firmness at cutting was monitored by the CHYMO-Graph® (patented tool by Chr. Hansen®), the firmness index at cutting was 6.5. After cutting, the curd was pre-stirred for 10 minutes before scalding at 41° C. The scalding took 30 min and afterwards the curd was stirred for 20 min before the whey off step. The pH of the curd at whey-off was between 6.20 and 6.25. Afterwards, the curd was formed into blocks and turned 3 times before milling. The pH at milling was 5.20 (±0.02). After the milling, the curd was salted with 2% of dry salt before stretching and cheese cooling.

Residual galactose measured in the cheeses after 5 weeks showed a reduction of 71.6% (6.7 mg/g using control strain CHCC9861, vs. 1.9 mg/g using the mix culture of CHCC27912 and CHCC27906).

After 30 days of storage (at 4° C.), the browning ability was compared by baking pizzas in a pizza oven for 3.5 min at 242° C. To prepare the pizzas, 40 g of tomato sauce was spread on the surface of frozen pizza dough and 135 g of coarse shredded cheese was distributed evenly on top. FIG. 3 herein shows an evident difference in browning between the reference CHCC9861 and the experimental culture with CHCC27912/CHCC27906.

Example 6: ST Ga/(+) Lac(−) Bacteria" of Step "(a) (II)"—M17 Criteria

*S. thermophilus* CHCC26980 was isolated as lactose negative mutant of the lactose positive wild type strain *S. thermophilus* CHCC5354.

Cells from CHCC5354 were UV-mutagenized with a UV-cross linker (Energy 120MJ). Cells which achieved a lethality of 99% (60 min UV-treatment) were plated on M17-lac agar plates containing X-Gal. Due to beta-galactosidase activity lactose positive colonies appear blue, whereas lactose negative mutants grow as white colonies.

With a start pH of 6.6 CHCC5354 and the lactose negative mutant CHCC26980 reached a final pH of 4.2, resp. 4.4, after 18 hours at 37° C. in milk with 2% sucrose added. CHCC5354 acidified in a similar way in milk without the addition of extra sugar, but the final pH for CHCC26980 in milk (without addition of sucrose) remained at 6.6 after 18 hours, showing that CHCC26980 is a lactose negative mutant.

The genome analysis of CHCC26980 revealed a mutation within the lacZ gene (deletion of one nucleotide A), resulting in a truncated lacZ gene which explains the lactose negative phenotype.

In a second step a galactose fermenting mutant was isolated from CHCC26980. Prior to the mutant isolation the strain was streaked on M17 agar plates with 2% galactose (M17-gal plates). Strain CHCC26980 did not grow significantly on galactose as sole carbohydrate source.

Overnight cultures were then plated on M17-gal plates and several colonies could be isolated after two days of growth at 37° C. Several mutants were purified on M17-gal plates and retested in M17 broth containing 2% galactose as sole carbohydrate. CHCC28149 was isolated as galactose positive mutant from CHCC26980 able to acidify to a pH of 5.0 after 16 hours in M17 broth with 2% galactose, whereas the pH of CHCC26980 decreased only minimal from a starting pH of 6.8 to 6.6.

Conclusion

The results demonstrate that the mutant CHCC28149 is a ST. Gal(+) Lac(−) bacterium, which complies with the criteria of (a)(II) of the separate aspect herein. The wild type ST. CHCC5354 strain is a ST. Gal(−) Lac(+) bacterium—i.e. it does not comply with the "not able to ferment lactose" criteria of (a)(II) of the separate aspect.

Example 7: Use of a Co-Culture of ST Gal(+) and ST Gal(+) Lac(−) Bacteria According to the Present Invention Gave a Higher % Reduction of Galactose in Milk as Compared to Use of ST Gal(+) Alone or Use of a Co-Culture of ST Gal(+) and ST Gal(+) Lac(+)

Fermentation of Milk

ST strains were grown as overnight culture in M17 broth (with 2% lactose for CHCC4323 and ST Gal(+)Lac(+) ref strain, and with 2% galactose for CHCC28149) to receive a fully grown culture. For the co-culture experiments the ST strains were inoculated 1% in milk (pasteurized at 98° C./30 min, 9.5% total solids) from the overnight cultures when grown alone. In mixed cultures the inoculation percentage was 0.75% for the lactose positive ST plus 0.25% for the ST Gal(+) Lac(−).

Incubation occurred for 16 hours at 37° C. At the end of fermentation samples were taken to measure galactose content in the fermented milk and with this the reduction of excreted galactose compared to the galactose negative reference strain CHCC4323.

The lactose negative S. thermophilus strain is not able to acidify the milk significantly. The strain can only grow on galactose excreted due to the lac/gal antiporter of lactose positive STs. Therefore they are "forced" to metabolize the available galactose. In the presence of both carbohydrates lactose and galactose as fermentable sugar the lactose is often preferred metabolized which would result in minor reduction of galactose at a specific time.

Results—Analysis of Acidification and Excreted Galactose in the Fermented Milk

The amounts of excreted galactose for the different tested strains are shown in Table 2 below:

Table 2 indicates the amount of galactose in milk and the reduction of galactose compared to the reference CHCC4323.

The addition of the lactose negative scavenger CHCC28149 leads to a reduction of galactose by 28% compared to the reference CHCC4323.

The addition of the lactose negative scavenger CHCC28149 to ST Gal(+)Lac(+) ref strain, which has already the good capacity to decrease galactose reduction by 20% compared to CHCC4323, leads to a reduction of galactose by 28%, compared to the reference CHCC4323. Compared to the use of ST Gal(+)Lac(+) ref strain the galactose content at the end of fermentation can thereby be reduced by additional 4%.

As a result the amount of free galactose is much lower when e.g. pizza cheese is produced with mixed cultures including the Lac(−) Gal(+) scavenger which is leading to reduced browning during baking.

TABLE 2

Average from two measurements from carbohydrate analysis. Results are shown in mg/g.

| Strain | Galactose | Galactose reduction (%) |
|---|---|---|
| CHCC4323 | 7.1 | 0 |
| ST Gal(+)Lac(+) ref strain | 5.4 | 24 |
| ST Gal(+)Lac(+) ref strain + CHCC28149 | 5.1 | 28 |

REFERENCES

1. Mukherjee et al (1994, J Dairy Sci 77:2839-2849)
2. Hassan et al. (International Journal of Food Microbiology 64 (2001) 199-203)
3. WO2011/026863A1 (Chr. Hansen)
4. WO2011/092300A1 (Chr. Hansen)
5. WO2013/160413A1 (Chr. Hansen)

The invention claimed is:

1. A method for producing a cheese with a reduced galactose content, comprising:
    (a) inoculating milk with:
        (I) Streptococcus thermophilus (ST) bacteria, wherein the ST bacteria are ST Gal(+) bacteria that reduce galactose content in milk by at least 10% as compared to reference ST strain CHCC4323 (deposited at Deutsche Sammlung von Mikroorganismen und Zellkulturen GmbH (DSMZ), under accession number DSM 32826), when assessed by inoculating skim cow milk with 1% overnight cultures of the ST bacteria, incubating for 18 hours at 37° C. to obtain fermented milk, and measuring galactose content in the fermented milk; and
        (II) Lactobacillus (Lb.) bacteria, wherein the Lb. bacteria comprise one or more Lb. bacteria selected from Lactobacillus delbrueckii subsp. lactis bacteria and Lb. helveticus bacteria and are Lb. Gal(+)Lac(−) bacteria that are able to ferment galactose but not able to ferment lactose, such that, when 1% overnight cultures of the Lb. bacteria are inoculated in De Man, Rogosa and Sharpe (MRS) medium containing 1% galactose as sole carbohydrate and incubated for 24 hours at 37° C., the pH of the medium has decreased by at least 0.5, and such that, when 1% overnight cultures of the Lb. bacteria are inoculated in MRS medium containing 1% lactose as sole carbohydrate and incubated for 18 hours at 37° C., the pH of the medium has not decreased by more than 1.0;
    (b) fermenting the milk with the bacteria of (a); and
    (c) processing the fermented milk to obtain cheese, wherein the cheese has a reduced galactose content.

2. The method of claim 1, wherein the cheese is a pasta filata cheese, a pizza cheese or a mozzarella cheese.

3. The method of claim 2, wherein the cheese is a mozzarella cheese.

4. The method of claim 1, wherein the ST bacteria reduce galactose content in milk by at least 30% as compared to reference ST strain CHCC4323.

5. The method of claim 1, wherein the ST bacteria comprise one or more strains selected from:
   (a) *Streptococcus thermophilus* strain CHCC19097 deposited with DSMZ under accession number DSM 32594;
   (b) *Streptococcus thermophilus* strain CHCC19100 deposited with DSMZ under accession number DSM 32595;
   (c) *Streptococcus thermophilus* strain CHCC27912 deposited with DSMZ under accession number DSM 32596;
   (d) *Streptococcus thermophilus* strain CHCC29526 deposited with DSMZ under accession number DSM 32597;
   (e) *Streptococcus thermophilus* strain CHCC29530 deposited with DSMZ under accession number DSM 32598; and
   (f) *Streptococcus thermophilus* strain CHCC14994 deposited with DSMZ under accession number DSM 25838.

6. The method of claim 1, wherein the milk is inoculated with from $10^4$ to $10^{14}$ cfu (colony forming units) of the ST bacteria per gram of the milk.

7. The method of claim 1, wherein the Lb. bacteria comprise *Lactobacillus delbrueckii* subsp. *lactis* bacteria.

8. The method of claim 1, wherein the Lb. bacteria exhibits galactose-fermenting properties such that, when 1% overnight cultures of the Lb. bacteria are inoculated in MRS medium containing 1% galactose as sole carbohydrate and incubated for 24 hours at 37° C., the pH of the medium has decreased by at least 0.9.

9. The method of claim 1, wherein the Lb. bacteria exhibits lactose-fermenting properties such that, when 1% overnight cultures of the Lb. bacteria are inoculated in MRS medium containing 1% lactose as sole carbohydrate and incubated for 18 hours at 37° C., the pH of the medium has not decreased by more than 0.3.

10. The method of claim 1, wherein the milk is inoculated with from $10^4$ to $10^{14}$ cfu (colony forming units) of the Lb. bacteria cells per gram of the milk.

11. The method of claim 1, wherein the fermentation time in step (b) is from 3 to 96 hours.

12. The method of claim 1, wherein the Lb. bacteria comprise *Lactobacillus delbrueckii* ssp. *lactis* strain CHCC27906, deposited with DSMZ under accession number DSM 32831.

13. The method of claim 1, wherein
   the ST bacteria comprise one or more strains selected from *Streptococcus thermophilus* strain CHCC19097 deposited with DSMZ under accession number DSM 32594; *Streptococcus thermophilus* strain CHCC19100 deposited with DSMZ under accession number DSM 32595; *Streptococcus thermophilus* strain CHCC27912 deposited with DSMZ under accession number DSM 32596; *Streptococcus thermophilus* strain CHCC29526 deposited with DSMZ under accession number DSM 32597; *Streptococcus thermophilus* strain CHCC29530 deposited with DSMZ under accession number DSM 32598; and *Streptococcus thermophilus* strain CHCC14994 deposited with DSMZ under accession number DSM 25838; and
   the Lb. bacteria comprise *Lactobacillus delbrueckii* ssp. *lactis* strain CHCC27906, deposited with DSMZ under accession number DSM 32831.

14. The method of claim 1, wherein the Lb. bacteria comprise *Lb. helveticus* bacteria.

* * * * *